United States Patent
Kishioka et al.

(10) Patent No.: US 9,822,330 B2
(45) Date of Patent: Nov. 21, 2017

(54) LIGHT-DEGRADABLE MATERIAL, SUBSTRATE, AND METHOD FOR PATTERNING THE SUBSTRATE

(71) Applicants: NISSAN CHEMICAL INDUSTRIES, LTD., Tokyo (JP); UNIVERSITY OF TOYAMA, Toyama-shi, Toyama (JP)

(72) Inventors: Takahiro Kishioka, Toyama (JP); Shigeo Kimura, Toyama (JP); Yoshiomi Hiroi, Toyama (JP); Yuki Usui, Toyama (JP); Hiromi Kitano, Toyama (JP); Tadashi Nakaji, Toyama (JP); Makoto Gemmei, Toyama (JP)

(73) Assignees: NISSAN CHEMICAL INDUSTRIES, LTD., Tokyo (JP); UNIVERSITY OF TOYAMA, Toyama-shi (JP)

( * ) Notice: Subject to any disclaimer, the term of this patent is extended or adjusted under 35 U.S.C. 154(b) by 298 days.

(21) Appl. No.: 14/435,342

(22) PCT Filed: Oct. 11, 2013

(86) PCT No.: PCT/JP2013/077804
§ 371 (c)(1),
(2) Date: Apr. 13, 2015

(87) PCT Pub. No.: WO2014/058061
PCT Pub. Date: Apr. 17, 2014

(65) Prior Publication Data
US 2015/0267159 A1    Sep. 24, 2015

(30) Foreign Application Priority Data
Oct. 11, 2012 (JP) ................ 2012-226380

(51) Int. Cl.
C12M 1/00 (2006.01)
G03F 7/075 (2006.01)
C08F 230/08 (2006.01)
C12M 1/12 (2006.01)

(52) U.S. Cl.
CPC .......... C12M 23/20 (2013.01); C08F 230/08 (2013.01); C12M 23/30 (2013.01); C12M 25/02 (2013.01); C12M 31/00 (2013.01); G03F 7/0757 (2013.01); *Y10T 428/24479* (2015.01); *Y10T 428/24802* (2015.01); *Y10T 428/31612* (2015.04); *Y10T 428/31663* (2015.04)

(58) Field of Classification Search
CPC ...... C08F 230/08; C12M 23/20; C12M 23/30; C12M 25/02; C12M 31/00; G03F 7/0757; Y10T 428/24479; Y10T 428/24802; Y10T 428/31612; Y10T 428/31663
USPC ....................................................... 435/180
See application file for complete search history.

(56) References Cited

FOREIGN PATENT DOCUMENTS

| JP | H03-7576 A | 1/1991 | |
| JP | 2006-006214 A | 1/2006 | |
| JP | 2007-039391 A | 2/2007 | |
| JP | 2008213177 | * 9/2008 | ............... B41N 1/14 |
| JP | 2008-268488 A | 11/2008 | |
| JP | 2009-065945 A | 4/2009 | |
| JP | 2012-034747 A | 2/2012 | |
| JP | 2012034747 A | * 2/2012 | ............. A61L 31/00 |
| WO | 2005/103227 A1 | 11/2005 | |

OTHER PUBLICATIONS

Kitano et al. (Carboxymethylbetaine copolymer layer covalently fixed to a glass substrate, Colloids and Surfaces B: Biointerfaces 94 (2012) 107-113, available online Feb. 1, 2012).*
Dec. 12, 2016 Office Action issued in Taiwanese Patent Application No. 102136769.
Nakanishi et al. "Spatiotemporal Control of Migration of Single Cells on a Photoactivatable Cell Microarray", Journal of the American Chemical Society, vol. 129, No. 21, pp. 6694-6695, 2007.
Nov. 19, 2013 Written Opinion issued in Application No. PCT/JP2013/077804.

* cited by examiner

Primary Examiner — Ling Choi
Assistant Examiner — Chun-Cheng Wang
(74) Attorney, Agent, or Firm — Oliff PLC

(57) ABSTRACT

There is provided a new material that can form a finer pattern and can be applied to adsorption/adhesion control of various cell species, proteins, viruses, and the like without the limitation of the light source. A light-degradable material comprising: a moiety that is capable of bonding to a surface of a substrate through a siloxane bond; and a structural unit of Formula (2-a) and/or Formula (2-b):

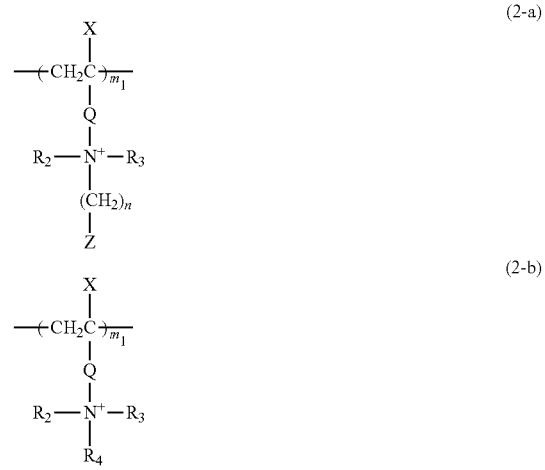

(where $R_2$ to $R_4$ are saturated linear alkyl groups; X is a hydrogen atom or an alkyl group; Z is a carbanion or a sulfo anion; Q is an ester bond group, a phosphodiester bond group, an amido bond group, an alkylene group, or an phenylene group or a combination of these divalent groups; $m_1$ is an integer of 1 to 200, and n is an integer of 1 to 10).

18 Claims, 1 Drawing Sheet

(A)　　　　　　　　　　　(B)

LIGHT-DEGRADABLE MATERIAL, SUBSTRATE, AND METHOD FOR PATTERNING THE SUBSTRATE

TECHNICAL FIELD

The present invention relates to a light-degradable material in which adsorption/adhesion of proteins, cells, viruses, and the like can be controlled by photo-patterning, a patterned substrate formed by using the material, and a method for producing the substrate.

BACKGROUND ART

In recent years, technologies (cell patterning) that define an adhesive region and a non-adhesive region of cells using a culture base material (or substrate) on which two chemical species, which are adhesive and non-adhesive to cells, are patterned have been studied in various fields from a cell biological fundamental researches to applied researches such as tissue engineering and cell substrate sensors.

Among the above technologies, various functional materials in which cell adhesion in a specific region on a culture substrate can be controlled by converting surface chemical species through phase transition, oxidation-reduction, and a chemical reaction according to external stimuli such as heat (temperature), electricity, and light have been studied in the technical field, which particularly attracts the attention, of converting (switching) the cell adhesion according to the external stimuli.

In Patent Document 1, for example, a material in which light-degradable groups and cell attachment controlling groups are sequentially bonded by covalent bonds has been developed as a cell attachment/culture base material that enables cell attachment properties to be applied by light irradiation. As other technologies, a method for fabricating a substrate to which cells intended for new cell adhesion patterning formation and size change are fixed during cell culture, including elimination of light-degradable protecting groups from functional groups by light irradiation (Patent Document 2), a patterning substrate for cell culture so that cells adhere onto a substrate in high-definition pattern and a method for producing the same (Patent Document 3), and a production method for a control tool of cell arrangement (Patent Document 4) have been developed.

PRIOR ART DOCUMENTS

Patent Documents

Patent Document 1: Japanese Patent Application Publication No. 2009-65945 (JP 2009-65945 A)
Patent Document 2: Japanese Patent Application Publication No. 2006-6214 (JP 2006-6214 A)
Patent Document 3: WO 2005/103227
Patent Document 4: Japanese Patent Application Publication No. 3-7576 (JP 3-7576 A)

SUMMARY OF THE INVENTION

Problem to be Solved by the Invention

As described in above Patent Documents, in the functional materials for controlling cell attachment by light irradiation, which have been developed, materials applied to adhesion control and the target of the adhesion control (cells and the like) are limited because the light exposure source for the light irradiation is a high-pressure mercury lamp or i line (wavelength 365 nm). In addition, in the light source that has been conventionally used, the formed pattern sizes are limited to the micrometer order ($10^{-6}$ m).

The present invention has been devised in view of the problems described above. An object of the present invention is to provide a new material that can form a finer pattern and can be applied to adsorption/adhesion control of various cell species, proteins, viruses, and the like without the limitation of the light source. Another object of the present invention is to provide a substrate patterned using the material and a method for producing the same.

Means for Solving the Problem

The inventors of the present invention have intensively studied in order to achieve the objects and thus have found that a zwitterionic polymer having a betaine structure changes adsorption/adhesion of cells, proteins, viruses, and the like by irradiation with ArF (argon fluoride) (wavelength 193 nm), which is also used for ultrafine fabrication of semiconductor production, and have accomplished the present invention.

As a first aspect, the present invention relates to a light-degradable material comprising: a structure of Formula (1):

$$(R_1O)_3\text{—Si—Y—} \quad (1)$$

(where $R_1$ is a saturated linear $C_{1-5}$ alkyl group;
and Y is a sulfur atom, a dithiocarbonic acid ester bond group (—S—C(═S)—), a trithiocarbonic acid ester bond group (—S—C(═S)—S—), a $C_{1-10}$ alkylene group, or an optionally substituted phenylene group or a combination of these divalent groups); a reaction starting terminal that is capable of bonding to a surface of a substrate through a siloxane bond; and a linking part linked to the reaction starting terminal and including a structural unit of Formula (2-a) and/or Formula (2-b):

(2-a)

(2-b)

(where $R_2$ to $R_4$ are each independently a saturated linear $C_{1-5}$ alkyl group;
X is a hydrogen atom or a saturated linear $C_{1-5}$ alkyl group;
Z is a carbanion (—COO⁻ group) or a sulfo anion (—SO$_3^-$ group);
Q is an ester bond group (—C(═O)—O— or —O—C(═O)—), a phosphodiester bond group (—O—P(═O)

(—O⁻)—O—), an amido bond group (—NH—CO— or —CO—NH—), a $C_{1-10}$ alkylene group, or an optionally substituted phenylene group or a combination of these divalent groups;

$m_1$ is an integer of 1 to 200, and n is an integer of 1 to 10).

As a second aspect, the present invention relates to a light-degradable material comprising: a polymer including a structural unit of Formula (2-a) and/or Formula (2-b) and a structural unit of Formula (3) having a side chain being capable of bonding to a surface of a substrate through a siloxane bond,

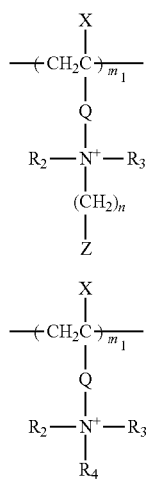

(where $R_2$ to $R_4$ are each independently a saturated linear $C_{1-5}$ alkyl group;

X is a hydrogen atom or a saturated linear $C_{1-5}$ alkyl group;

Z is a carbanion (—COO⁻ group) or a sulfo anion (—SO₃⁻ group);

Q is an ester bond group (—C(═O)—O— or —O—C(═O)—), a phosphodiester bond group (—O—P(═O)(—O⁻)—O—), an amido bond group (—NH—CO— or —CO—NH—), a $C_{1-10}$ alkylene group, or an optionally substituted phenylene group or a combination of these divalent groups;

$m_1$ is an integer of 1 to 200; and n is an integer of 1 to 10).

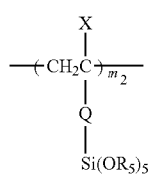

(where $R_5$ is a saturated linear $C_{1-5}$ alkyl group;

X is a hydrogen atom or a saturated linear $C_{1-5}$ alkyl group;

Q is an ester bond group (—C(═O)—O— or —O—C(═O)—), a phosphodiester bond group (—O—P(═O)(—O⁻)—O—), an amido bond group (—NH—CO— or —CO—NH—), a $C_{1-10}$ alkylene group, or an optionally substituted phenylene group or a combination of these divalent groups; and $m_2$ is an integer of 1 to 200).

As a third aspect, the present invention relates to the light-degradable material according to the first aspect or the second aspect, in which the light-degradable material is a material for pattern formation by photolithography.

As a fourth aspect, the present invention relates to the light-degradable material according to the third aspect, in which the photolithography is carried out using an ArF excimer laser.

As a fifth aspect, the present invention relates to the light-degradable material according to the fourth aspect, in which any one of or both of Y and Q include an optionally substituted phenylene group.

As a sixth aspect, the present invention relates to the light-degradable material according to any one of the third aspect to the fifth aspect, in which the light-degradable material is a material for forming a pattern in which proteins, cells, or viruses are specifically adsorbed on the surface of the substrate.

As a seventh aspect, the present invention relates to a substrate that is capable of forming a pattern, obtained by bonding the light-degradable material as described in any one of the first aspect to the sixth aspect to a surface of the substrate through siloxane bonds.

As an eighth aspect, the present invention relates to the substrate according to the seventh aspect, in which the substrate is a substrate on which a pattern is formed by carrying out pattern exposure on the light-degradable material bonded to the surface of the substrate by a photolithography method.

As a ninth aspect, the present invention relates to the substrate according to the eighth aspect, in which the exposure is carried out using an ArF excimer laser.

As a tenth aspect, the present invention relates to the substrate according to any one of the seventh aspect to the tenth aspect, in which the substrate is a glass substrate, a metal substrate, a metal oxide substrate, a metal nitride substrate, a metal carbide substrate, a metal oxynitride substrate, a ceramic substrate, a silicon substrate, a silicon oxide substrate, a silicon nitride substrate, a silicon carbide substrate, a silicon oxynitride substrate, or a silicon substrate.

As an eleventh aspect, the present invention relates to a substrate for cell culture, made by using the substrate as described in any one of the seventh aspect to the tenth aspect.

As a twelfth aspect, the present invention relates to a microflow channel made by using the substrate as described in any one of the seventh aspect to the tenth aspect.

As a thirteenth aspect, the present invention relates to a method of producing a patterned substrate to which proteins, cells, or viruses are specifically adsorbed, the method comprising:

producing a surface-modified substrate by fixing the light-degradable material as described in any one of the first aspect to the sixth aspect to a surface of the substrate through siloxane bonds;

forming a pattern on the surface of the substrate by carrying out pattern exposure on the surface-modified substrate; and carrying out adsorption/adhesion of proteins, cells, or viruses on a part where the pattern exposure has been carried out.

As a fourteenth aspect, the present invention relates to the method for producing the patterned substrate according to the thirteenth aspect, in which the pattern exposure is carried out using an ArF excimer laser.

As a fifteenth aspect, the present invention relates to the method for producing the patterned substrate according to the thirteenth aspect or the fourteenth aspect, in which the pattern formed substrate is a substrate for cell culture.

As a sixteenth aspect, the present invention relates to the method for producing the patterned substrate according to the thirteenth aspect or the fourteenth aspect, in which the pattern formed substrate is a substrate for microflow channel formation.

Effects of the Invention

In the light-degradable material of the present invention, an anion part in a zwitterion is disconnected by light irradiation, particularly by ArF irradiation to change its structure from a zwitterion polymer chain to a cationic polymer chain, or a phenyl group or the like is degraded to lose the zwitterion polymer chain when the phenyl group or the like is contained in the material. This enables proteins, cells, viruses, and the like to be adsorbed on/adhere onto the degraded part, and thus the light-degradable material is a material in which the adsorption/adhesion of proteins and the like can be controlled.

In the substrate of the present invention, the light-degradable material is strongly bonded to the surface of the substrate through siloxane bonds. Only the light-irradiated part of the light-degradable material is degraded by exposing the substrate to light through a mask or the like and thus the adsorption/adhesion to the proteins and the like is easily provided to the light-irradiated part alone. Further, in the light-degradable material, an ultrafine pattern in the nanometer order ($10^{-9}$ m) can be formed by ArF exposure. Therefore, the present invention can provide a substrate that enables the proteins and the like to be adsorbed on/adhere onto the ultrafine pattern alone by light irradiation through a mask having a desired shape. This is particularly useful for forming the pattern to which proteins or viruses having a size of an order of nanometers are specifically adsorbed.

According to the production method of the patterned substrate of the present invention, a substrate to which the proteins and the like are absorbed on/adhere onto a desired pattern shape can be easily produced.

As described above, the present invention provides a new method useful for cell biological fundamental researches, tissue engineering, or cell substrate sensors.

BRIEF DESCRIPTION OF THE DRAWINGS

FIG. 3A is an observation photograph and FIG. 3B is a schematic view.

MODES FOR CARRYING OUT THE INVENTION

[Light-Degradable Material]

Figure 1:
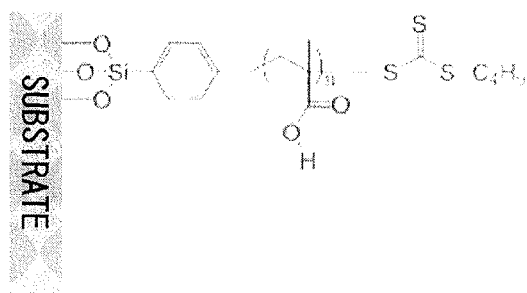
FIG. 1 is a schematic view illustrating a surface-modified substrate produced in Comparative Example 1.

The light-degradable material of the present invention is a material constituted by a reaction starting terminal of Formula (1) that is capable of bonding to the substrate described below through a siloxane bond and a linking part linked to the reaction starting terminal and including a structural unit of Formula (2-a) and/or Formula (2-b).

The light-degradable material of the present invention also may be a material including a polymer including a structural unit of Formula (2-a) and/or Formula (2-b) and a structural unit of Formula (3) having a side chain being capable of bonding to the surface of the substrate through a siloxane bond.

(where $R_1$ is a saturated linear $C_{1-5}$ alkyl group; and
Y is a sulfur atom, a dithiocarbonic acid ester bond group (—S—C(=S)—), a trithiocarbonic acid ester bond group (—S—C(=S)—S—), a $C_{1-10}$ alkylene group, or an optionally substituted phenylene group or a combination of these divalent groups);

(where $R_2$ to $R_4$ are each independently a saturated linear $C_{1-5}$ alkyl group;
X is a hydrogen atom or a saturated linear $C_{1-5}$ alkyl group; Z is a carbanion (—COO$^-$ group) or a sulfo anion (—SO$_3^-$ group);
Q is an ester bond group (—C(=O)—O— or —O—C(=O)—), a phosphodiester bond group (—O—P(=O)(—O—)—O—), an amido bond group (—NH—CO— or —CO—NH—), a $C_{1-10}$ alkylene group, or an optionally substituted phenylene group or a combination of these divalent groups;
$m_1$ is an integer of 1 to 200; and
n is an integer of 1 to 10); and

(where $R_5$ is a saturated linear $C_{1-5}$ alkyl group;
X is a hydrogen atom or a saturated linear $C_{1-5}$ alkyl group;
Q is an ester bond group (—C(=O)—O— or —O—C(=O)—), a phosphodiester bond group (—O—P(=O)(—O$^-$)—O—), an amido bond group (—NH—CO— or —CO—NH—), a $C_{1-10}$ alkylene group, or an optionally substituted phenylene group or a combination of these divalent groups; and $m_2$ is an integer of 1 to 200).

In Formula (1), Formula (2-a), Formula (2-b), or Formula (3), examples of the saturated linear $C_{1-5}$ alkyl group in $R_1$ to $R_5$ and X may include a methyl group, an ethyl group, an n-propyl group, an i-propyl group, an n-butyl group, an i-butyl group, a s-butyl group, a t-butyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, and an n-pentyl group. Preferably, the saturated linear $C_{1-5}$ alkyl group is the methyl group, the ethyl group, the n-propyl group, the n-butyl group, and the n-pentyl group.

Examples of the $C_{1-10}$ alkylene group in Y and Q may include a methylene group, an ethylene group, an n-propylene group, an isopropylene group, a cyclopropylene group, an n-butylene group, an isobutylene group, a sec-butylene group, a tert-butylene group, a cyclobutylene group, a 1-methyl-cyclopropylene group, a 2-methyl-cyclopropylene group, an n-pentylene group, a 1-methyl-n-butylene group, a 2-methyl-n-butylene group, a 3-methyl-n-butylene group, a 1,1-dimethyl-n-propylene group, a 1,2-dimethyl-n-propylene group, a 2,2-dimethyl-n-propylene group, a 1-ethyl-n-propylene group, a cyclopentylene group, a 1-methyl-cyclobutylene group, a 2-methyl-cyclobutylene group, a 3-methyl-cyclobutylene group, a 1,2-dimethyl-cyclopropylene group, a 2,3-dimethyl-cyclopropylene group, a 1-ethyl-cyclopropylene group, a 2-ethyl-cyclopropylene group, an n-hexylene group, a 1-methyl-n-pentylene group, a 2-methyl-n-pentylene group, a 3-methyl-n-pentylene group, a 4-methyl-n-pentylene group, a 1,1-dimethyl-n-butylene group, a 1,2-dimethyl-n-butylene group, a 1,3-dimethyl-n-butylene group, a 2,2-dimethyl-n-butylene group, a 2,3-dimethyl-n-butylene group, a 3,3-dimethyl-n-butylene group, a 1-ethyl-n-butylene group, a 2-ethyl-n-butylene group, a 1,1,2-trimethyl-n-propylene group, a 1,2,2-trimethyl-n-propylene group, a 1-ethyl-1-methyl-n-propylene group, a 1-ethyl-2-methyl-n-propylene group, a cyclohexylene group, a 1-methyl-cyclopentylene group, a 2-methyl-cyclopentylene group, a 3-methyl-cyclopentylene group, a 1-ethyl-cyclobutylene group, a 2-ethyl-cyclobutylene group, a 3-ethyl-cyclobutylene group, a 1,2-dimethyl-cyclobutylene group, a 1,3-dimethyl-cyclobutylene group, a 2,2-dimethyl-cyclobutylene group, a 2,3-dimethyl-cyclobutylene group, a 2,4-dimethyl-cyclobutylene group, a 3,3-dimethyl-cyclobutylene group, a 1-n-propyl-cyclopropylene group, a 2-n-propyl-cyclopropylene group, a 1-isopropyl-cyclopropylene group, a 2-isopropyl-cyclopropylene group, a 1,2,2-trimethyl-cyclopropylene group, a 1,2,3-trimethyl-cyclopropylene group, 2,2,3-trimethyl-cyclopropylene group, a 1-ethyl-2-methyl-cyclopropylene group, a 2-ethyl-1-methyl-cyclopropylene group, a 2-ethyl-2-methyl-cyclopropylene group, and a 2-ethyl-3-methyl-cyclopropylene group. The preferable $C_{1-10}$ alkylene group is a methylene group, an ethylene group, an n-propylene group, an i-propylene group, an n-butylene group, an i-butylene group, a sec-butylene group, and a tert-butylene group.

When one or both of Y and Q is/are phenylene groups, the phrase "optionally substituted" means that the hydrogen atom of the phenylene group can be substituted with the saturated linear $C_{1-5}$ alkyl group, a halogen atom (a fluorine atom, a chlorine atom, a bromine atom, or an iodine atom), or a hydroxy group.

In Formula (1), Y preferably contains phenylene groups that allow the light-degradable material to be degraded (to form a pattern) in a lower exposed amount, that is, to achieve high sensitivity, when the pattern is formed by exposure after fixing the light-degradable material on the substrate described below. The hydrogen atom of the phenylene group is optionally substituted with the saturated linear $C_{1-5}$ alkyl group, a halogen atom (a fluorine atom, a chlorine atom, a bromine atom, or an iodine atom), or a hydroxy group.

In Formula (2-a), Z is preferably a carbanion (—COO$^-$ group) or a sulfo anion (—SO$_3^-$ group).

In Formula (2-a), Formula (2-b), and Formula (3), Q is preferably a combination of an ester bond group (—C(=O)—O— or —O—C(=O)—) and a $C_{1-10}$ alkylene group or a combination of a phosphodiester bond group (—O—P(=O)(—O$^-$)—O—) and a $C_{1-10}$ alkylene group.

The structural unit (2-a) is preferably a structural unit derived from a monomer of Formula (2-a-1), for example.

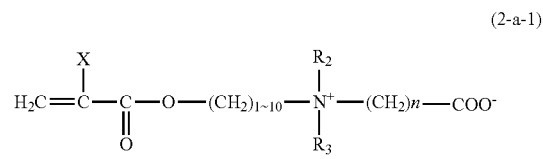

(2-a-1)

In Formula (2-a-1), $R_2$, $R_3$, X, and n are the same as defined above.

Specific examples of the monomer of Formula (2-a-1) may include N-(meth)acryloyloxymethyl-N,N-dimethylammonium-α-N-methylcarboxybetaine, N-(meth)acryloyloxyethyl-N,N-dimethylammonium-α-N-methylcarboxybetaine, N-(meth)acryloyloxypropyl-N,N-dimethylammonium-α-N-methylcarboxybetaine, N-(meth)acryloyloxymethyl-N,N-diethylammonium-α-N-methyl-carboxybetaine, N-(meth)acryloyloxyethyl-N,N-diethylammonium-α-N-methylcarboxybetaine, and N-(meth)acryloyloxypropyl-N,N-diethylammonium-α-N-methyl-carboxybetaine. These monomers can be used singly or in combination of two or more of them. Among them, N-methacryloyloxyethyl-N,N-dimethylammonium-α-N-methylcarboxybetaine is particularly preferably used.

A compound in which the carbanion (—COO$^-$ group) moiety in Formula (2-a-1) is substituted with the sulfo anion (—SO$_3^-$ group) is also preferably used. Examples of the compound include N-(3-sulfopropyl)-N-(meth)acryloyloxyethyl-N,N-dimethylammoniumbetaine.

Examples of the structural unit of Formula (2-b) may include structural units derived from monomers such as 2-((meth)acryloyloxy)ethyl-2'-(trimethylammonio)ethyl phosphate, 3-((meth)acryloyloxy)propyl-2'-(trimethylammonio)ethyl phosphate, 4-((meth)acryloyloxy)butyl-2'-(trimethylammonio)ethyl phosphate, 5-((meth)acryloyloxy)pentyl-2'-(trimethylammonio)ethyl phosphate, 6-((meth)acryloyloxy)hexyl-2'-(trimethylammonio)ethyl phosphate, 2-((meth)acryloyloxy)propyl-2'-(trimethylammonio)ethyl phosphate, 2-((meth)acryloyloxy)butyl-2'-(trimethylammonio)ethyl phosphate, 2-((meth)acryloyloxy)pentyl-2'-(trimethylammonio)ethyl phosphate, 2-((meth)acryloyloxy)hexyl-2'-(trimethylammonio)ethyl phosphate, and 2-methacryloyloxyethyl phosphorylcholine (MPC). Among them, the structural unit derived from 2-methacryloyloxyethyl phosphorylcholine (MPC) is particularly preferable.

The structural unit (3) is preferably a structural unit derived from a monomer of Formula (3-1).

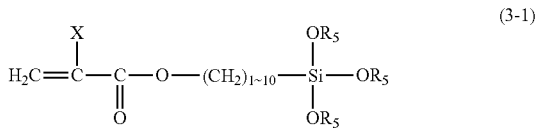

In Formula (3-1), $R_5$ and X are the same as defined in Formula (3). Specific examples of the monomer of Formula (3-1) may include γ-(meth)acryloyloxypropyltrimethoxysilane, γ-(meth)acryloyloxypropyltriethoxysilane, and γ-(meth)acryloyloxypropyltriisopropoxysilane.

The structural unit (3) may be a monomer including a phenylene group such as styryltrimethoxysilane and a monomer such as 3-methacryloyloxypropyltrimethoxysilane.

The light-degradable material of the present invention is suitable for a material for pattern formation and particularly suitable for the material for pattern formation by photolithography using an ArF excimer laser as exposure light.

The light-degradable material of the present invention is suitable for a material for forming a pattern to which proteins, cells, or viruses are specifically adsorbed on the surface of the substrate because the light-degradable material exerts adsorption/adhesion to proteins, cells, or viruses by exposure.

[Production Method of Substrate and Patterned Substrate]

The present invention also relates to production methods of a substrate on which a pattern can be formed by bonding the light-degradable material to the surface of the substrate through siloxane bonds, a patterned substrate formed by carrying out pattern exposure on the light-degradable material bonded onto the surface of the substrate, and a patterned substrate on which proteins, cells, and viruses are specifically adsorbed.

The patterned substrate can be produced by the following (a) to (c) steps.

(a) a step of producing a surface-modified substrate by fixing the light-degradable material to the surface of the substrate through siloxane bonds;

(b) a step of forming a pattern on the surface of the substrate by carrying out the pattern exposure on the surface-modified substrate; and (c) a step of adsorbing proteins, cells, or viruses to a part where the pattern exposure is carried out.

The step (a) is a step of fixing the light-degradable material of the present invention on the surface of the substrate, that is, a step of forming the coating film of the light-degradable material on the surface of the substrate.

The substrate used here preferably contains hydroxy groups on its surface so that the light-degradable material can be bonded to the substrate through siloxane bonds. Suitable examples of the substrate may include a glass substrate, a metal, a metal oxide substrate, a metal nitride, a metal carbide, a metal oxynitride, a ceramic substrate, a silicon substrate, silicon oxide, silicon nitride, silicon carbide, and silicon oxynitride. When a substrate having no hydroxy groups on its surface is used, the surface is preferably hydrophilized.

Examples of methods for fixing the light-degradable material of the present invention to the surface of the substrate (for forming a coating film on the surface of the substrate) may include a spin coating method, a flow coating method, a spray coating method, a dipping method, a brushing method, a roll coating method, and a vapor deposition method. The present invention, however, is not limiting to those examples.

In general, the atmosphere for the step may be in the air atmosphere. In general, the temperature when the light-degradable material of the present invention is applied onto the surface of the substrate may be room temperature or may be warm temperature. Preferably, the amount of the light-degradable material fixed on the surface of the substrate is appropriately adjusted depending on the application of the substrate.

After the light-degradable material is fixed on the surface of the substrate (after the coating film is formed on the surface of the substrate), the substrate is preferably heated from the viewpoint of increasing production efficiency. Although the heating temperature at the time of heating the substrate is not uniformly determined because the heating temperature varies depending on the allowable temperature limit of the substrate and other factors, generally a temperature suitable for the substrate is preferably selected in a range of 30° C. to 150° C.

Alternatively, the step of fixing the light-degradable material of the present invention on the surface of the substrate can be achieved by firstly bonding the reaction starting terminal having a structure of Formula (1) onto the surface of the substrate, and thereafter polymerizing a monomer deriving the structural unit of Formula (2-a) and/or Formula (2-b) from the reaction starting terminal to form a light-degradable material on the surface of the substrate.

In this case, the reaction starting terminal having the structure of Formula (1) is bonded to the substrate and thereafter a group that easily causes chain transfer reaction is introduced. Then, a monomer deriving the structural unit of Formula (2-a) and/or Formula (2-b), a polymerization initiator, a chain transfer agent, and the like are charged and reacted to form the light-degradable material of the present invention in which a polymer having the structural unit of Formula (2-a) and/or Formula (2-b) is bonded to the reaction starting terminal group. This method is called a "Grafting from" method (surface-initiated graft polymerization).

This method allows a functional material to exist at a high density on the surface of the substrate in the state of relatively thin film and to improve desired functions in comparison with the method for applying the light-degradable material onto the surface of the substrate. For example, in this application, the contrast of a pattern can be enhanced by improving adhesion of proteins, cells, and viruses to the exposed part. Typically, thus fabricated material is also called a "polymer brush". A "Grafting to" method carried out by reaction of an existing macromolecular compound and functional groups on the surface of the substrate may also be used.

Examples of the polymerization initiator used in the reaction may include azobisisobutyronitrile, azoisobutyronitrile, methyl azoisobutyrate, azobisdimethylvaleronitrile, 2,2'-azobis(2-methylpropionamidine)dihydrochloride, benzoyl peroxide, potassium persulfate, ammonium persulfate, benzophenone derivatives, phosphine oxide derivatives, benzoketone derivatives, phenyl thioether derivative, azide derivatives, diazo derivatives, and disulfide derivatives. The present invention, however, is not limiting to those examples. These polymerization initiators may be used singly or in combination of two or more of them.

The amount of the polymerization initiator is not particularly limited. In general, the amount is preferably about 0.01 part by mass to 10 parts by mass per 100 parts by mass of the monomer component.

The chain transfer agent used in the reaction can be used by mixing with the monomer component. Examples of the chain transfer agent may include mercaptan group-containing compounds such as lauryl mercaptan, dodecyl mercaptan, and thioglycerol and inorganic salts such as sodium hypophosphite and sodium bisulfate. The present invention, however, is not limited to those examples. These chain transfer agents may be used singly or in combination of two or more of them.

The amount of the chain transfer agent is not particular limited. In general, the amount is preferably about 0.01 part by mass to 10 parts by mass per 100 parts by mass of the monomer component.

An example of a method for polymerizing the monomer component may include a solution polymerization method. The present invention, however, is not limited to the example.

Examples of a solvent used in the solution polymerization method may include alcohols such as methanol, ethanol, isopropanol, ethylene glycol, propylene glycol, and trifluoroethanol; ketones such as acetone and methyl ethyl ketone; ethers such as diethyl ether and tetrahydrofuran, aromatic hydrocarbon compounds such as benzene, toluene, and xylene; aliphatic hydrocarbon compounds such as n-hexane; alicyclic hydrocarbon compounds such as cyclohexane, and acetic acid esters such as methyl acetate and ethyl acetate. The present invention, however, is not limited to those examples. These solvents may be used singly or in combination of two or more of them.

In general, the amount of the solvent is preferably adjusted so that the concentration of the monomer component in a solution obtained by dissolving the monomer component into the solvent is about 1% by mass to about 80% by mass.

Preferably, polymerization conditions such as a polymerization temperature and a polymerization time when the monomer component is polymerized are appropriately adjusted according to the composition of the monomer component, the type and the amount of the polymerization initiator.

The atmosphere when the monomer component is polymerized is preferably inert gas. Examples of the inert gas may include nitrogen gas and argon gas. The present invention, however, is not limited to those examples.

Subsequently, the step (b) is a step of forming a pattern by carrying out pattern exposure on the surface of the substrate to which the light-degradable material of the present invention produced in the step (a) is bonded by photolithography. This step is preferably carried out using an ArF excimer laser (wavelength: 193 nm) as exposure light through a pattern mask. As an exposure device, an ArF stepper for ultrafine exposure for semiconductor production or the like can be used.

An exposed amount can be appropriately selected from 10 mJ to about 3,000 mJ and an exposed amount of 250 mJ or more is more preferable.

Proteins, cells, or viruses can be adsorbed on or adhere onto a cationic part or a zwitterion lost part (that is, an exposed part) of the substrate thus obtained because the zwitterion polymer chain of the light-degradable material in the exposed part is changed to the cationic polymer in structures, or the zwitterion is lost due to degradation.

Finally, as the step (C), proteins, cells, or viruses are adsorbed on the pattern-exposed part to obtain the substrate with the pattern formed by specifically adsorbing the proteins, the cells, or the viruses. Examples of the method may include an incubation method.

The patterned substrate of the present invention can be suitably applied for a substrate for cell culture and a substrate for microflow channel formation.

EXAMPLES

Hereinafter, the present invention will be more specifically described with reference to Examples. The present invention, however, is not limited to the following Examples.

The weight average molecular weights (Mw) of polymers described in the following Production Examples in this specification are measured results obtained by a gel permeation chromatography (GPC) method. Measurement conditions for measurements using a GPC device are as follows:
GPC column: WB-G-50 (manufactured by Wako Pure Chemical Industries, Ltd.)
Column temperature: 25° C.
Solvent: 0.1 M aqueous NaBr solution
Flow rate: 0.2 mL/minute
Standard sample: Pullulan (manufactured by Showa Denko K.K.)

Example 1: Production of Surface-Modified Silicon Wafer with Zwitterionic Polymer Chain (B-PCMB-Modified Substrate)

Production Example 1 Synthesis of SDTB (Sodium Dithiobenzoate)

Sodium methoxide (1.08 g, 0.020 mol) was dissolved in 3.6 mL of degassed methanol, and the elemental sulfur (650 mg, 0.020 mol) was added to the methanol solution. The resultant mixture was stirred while $N_2$ bubbling (nitrogen purge) was carried out. Benzyl chloride (1.14 mL, 0.010 mol) was added dropwise to the mixture over 30 minutes and the resultant mixture was reacted at 65° C. for 10 hours (Scheme 1).

After completion of the reaction, the reaction system was immersed in iced water. The precipitated salt was removed by suction filtration and the solvent was removed by vacuum concentration. To the residue, 10 mL of water was added and suction filtration was carried out again. Thereafter, 4 mL of diethyl ether was added to the filtrate to carry out a liquid separation operation. Further the liquid separation operation was carried out two times in the same manner as above. To the collected aqueous phase, 4 mL of diethyl ether and 5 mL of 1 M HCl were added to carry out a liquid separation operation. To the collected ether phase, 6 mL of water and 6 mL of 1 M NaOH were added to carry out a liquid separation operation. After the liquid separation operation, a liquid separation operation of adding diethyl ether and 1M HCl to the collected aqueous phase and a liquid separation operation of adding water and 1M NaOH in the collected ether phase were further carried out two times in the same procedure as above.

The collected aqueous phase was concentrated under reduced pressure and the residue was added dropwise to acetone. The precipitated salt was removed by suction filtration and the filtrate was dried under reduced pressure to obtain brown powder product SDTB (A) (sodium dithiobenzoate) (yield amount: 542 mg).

Scheme 1

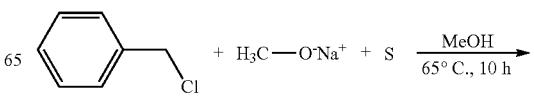

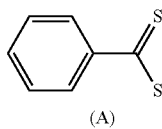

(A)

Production Example 2 Synthesis of BSTMPA (2-(n-butylthio(thiocarbonyl)thio)-2-methyl-propionic acid)

Potassium phosphate (4.25 g, 20 mmol) was dissolved in 32 mL of acetone and the solution was stirred for 30 minutes. Thereafter, 2.14 mL of 1-butanethiol, then 3.0 mL of carbon disulfide, and then 3.34 g of 2-methyl-2-bromopropionic acid were sequentially added at 10-minute intervals. The mixture was reacted for 18 hours (Scheme 2).

After the reaction mixture was purified with a silica gel column chromatography, the solvent was removed by vacuum concentration and the residue was dissolved in hexane. Thereafter, the solution was cooled to collect a solid. The collected solid was dried in a desiccator to obtain BSTMPA (B) as a yellow power (yield amount: 840 mg).

Scheme 2

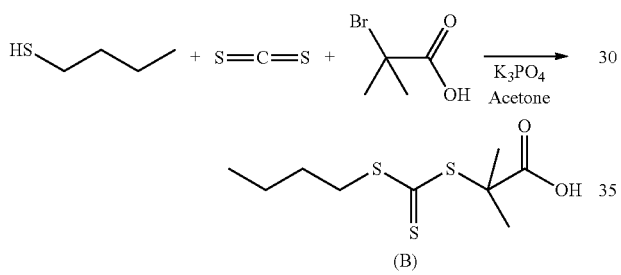

Production Example 3 Surface Modification of Silicon Wafer

An 8-inch silicon wafer was washed with water, methanol, and acetone in this order and cleaned by UV/ozone.

Into a reaction container that can contain the 8-inch silicon wafer, a solution in which 185 µL (2 v/v %) of CMPS (4-(chloromethyl)phenyltrimethoxysilane) was dissolved into 9 mL of toluene was charged and the washed silicon wafer was immersed into the solution under nitrogen atmosphere. The reaction container was placed in an oil bath of 80° C. for 15 hours to react hydroxy groups on the surface of the silicon wafer with alkoxysilyl groups of 4-(chloromethyl)phenyltrimethoxysilane. Thereafter, the silicon wafer that was taken out was washed with toluene two times and then washed for 30 seconds using ultrasonic waves, followed by further being washed with toluene two times. After washing, the silicon wafer was dried with flowing $N_2$ to obtain the silicon wafer whose surface was modified with CMPS (refer to Scheme 3: upper part).

Production Example 4 Surface Modification of Silicon Wafer with Zwitterionic Polymer Chains (Polymer Brush Type)

After 20 mg of SDTB obtained in Production Example 1 was dissolved in 10 mL of tetrahydrofuran (THF), the silicon wafer whose surface was modified with CMPS obtained in Production Example 3 was immersed into this solution and reacted at room temperature for 1 hour (refer to Scheme 3: middle part).

Thereafter, the silicon wafer was washed with THF and methanol and dried with flowing $N_2$.

The silicon wafer whose surface was modified with dithiobenzoate as described above was placed in a sample bottle. Into this bottle, ethanol (10.00 mL) and N-methacryloyloxyethyl-N,N-dimethylammonium-α-N-methyl-carboxybetaine (CMB, 2.33 g, 10 mmol) was added and the resultant solution was bubbled with $N_2$ for 30 minutes or more. Subsequently, BSTMPA (B) (50.4 mg, 0.20 mmol) obtained in Production Example 2 and the water-soluble azo polymerization initiator V-501 (2,2'-azobis(2-methylpropionamidine)dihydrochloride, manufactured by Wako Pure Chemical Industries Ltd., 11.2 mg, 0.040 mmol) were added to the reaction solution. The resultant reaction solution was bubbled with $N_2$ for 3 minutes and the sample bottle was sealed. The sample bottle was placed in an oil bath of 70° C. and polymerization reaction was carried out for 24 hours (refer to Scheme 3: lower part).

After completion of the polymerization reaction, the silicon wafer was washed with methanol two times, water one time, and further methanol one time, and dried with flowing $N_2$ to obtain the silicon wafer whose surface was modified with CMB polymer chains serving as zwitterionic polymer chains.

The structure formula of the CMB polymer chain illustrated in Scheme 3: lower part is one of the presumed structures of the CMB polymer chain obtained in Production Example 4.

Scheme 3

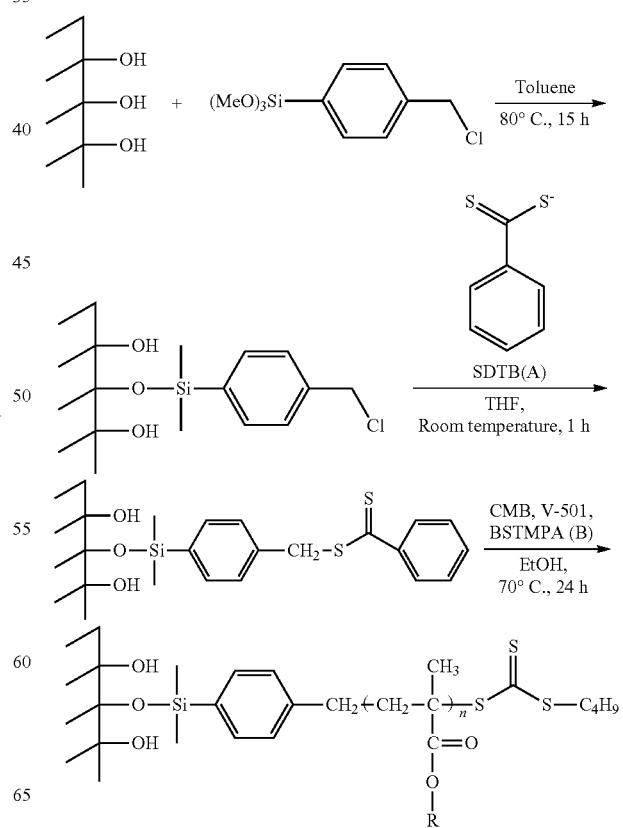

R = 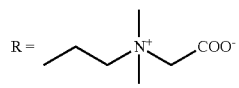

Example 2: Production of Surface-Modified Silicon Wafer with Zwitterionic Polymer Chain (BTPT-g-PCMB-Modified Substrate)

Production Example 5 Substrate Modification with BTPT (S-benzyl-S'-trimethoxysilylpropyltrithiocarbonate)

To 200 mL of toluene, 2.8 g of S-benzyl-S'-trimethoxysilylpropyl trithiocarbonate (BTPT) solution serving as a silane coupling agent with the reversible addition-fragmentation chain transfer (RAFT) agent that can carry out RAFT polymerization was dissolved. An 8-inch silicon wafer washed in the same procedure as the procedure in Production Example 3 was immersed into the solution and was left to stand for 24 hours at room temperature to react hydroxy groups on the surface of the silicon wafer with trimethoxysilyl groups in BTPT. Thereafter, the silicon wafer that was taken out was washed with toluene and dried with flowing $N_2$ to obtain the silicon wafer modified with BTPT (refer to Scheme 4: upper part).

Production Example 6 Surface Modification of Silicon Wafer with Zwitterionic Polymer Chain (Polymer Brush Type)

To the sample bottle in which the silicon wafer (substrate) modified with BTPT in Production Example 5 was placed, ethanol (10.00 mL) and CMB (N-(meth)acryloyloxyethyl-N,N-dimethylammonium-α-N-methylcarboxybetaine, 2.33 g, 10 mmol) were added and the resultant solution was bubbled with $N_2$ for 30 minutes or more. Subsequently, BSTMPA (B) (50.4 mg, 0.20 mmol) synthesized in Production Example 2 and the water-soluble azo polymerization initiator V-501 (2,2'-azobis(2-methylpropionamidine)dihydrochloride, manufactured by Wako Pure Chemical Industries Ltd., 11.2 mg, 0.040 mmol) were added to the reaction solution. The resultant reaction solution was bubbled with $N_2$ for 3 minutes and the sample bottle was sealed. The sample bottle was placed in an oil bath of 70° C. and polymerization reaction was carried out for 24 hours (refer to Scheme 4: lower part).

After completion of the polymerization reaction, the silicon wafer was washed with methanol two times, water one time, and further methanol one time, and dried with flowing $N_2$ to obtain the silicon wafer modified with BTPT-g-PCMB.

BTPT-g-PCMB illustrated in Scheme 4: lower part is one of the presumed structures of BTPT-g-PCMB obtained in Production Example 6.

Scheme 4

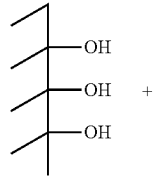

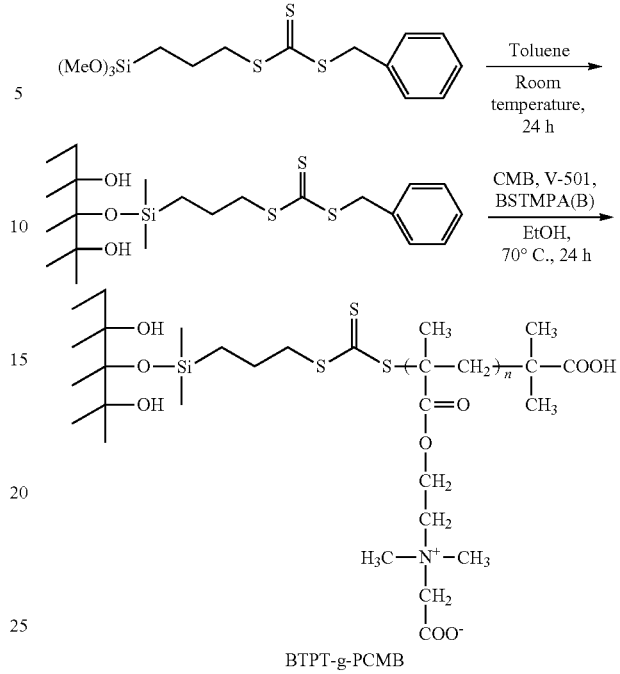

BTPT-g-PCMB

Example 3 Production of Surface-Modified Silicon Wafer with Zwitterionic Polymer Chain (SPB-KBM-1403 Copolymer-Modified Substrate)

Production Example 7 Synthesis of SPB-KBM-1403 Copolymer

KBM-1403 (p-styryltrimethoxysilane, manufactured by Shin-Etsu Chemical Co., Ltd.) (0.175 g, 0.78 mmol) and SPB (N-(3-sulfopropyl)-N-methacroyloxyethyl-N,N-dimethyl ammoniumbetaine, 1.96 g, 0.70 mmol) were added to nitrogen-bubbled THF (13.75 mL). Azobisisobutyronitrile (AIBN, 0.107 g, 0.65 mmol) was added to the mixture and the polymerization was started at 70° C. AIBN (0.0214 g, 0.13 mmol) was further added four hours later, and the reaction was further carried out for four hours to obtain a polymer having two structural units of Formula (4). The weight average molecular weight of the obtained polymer was 105,000.

(4)

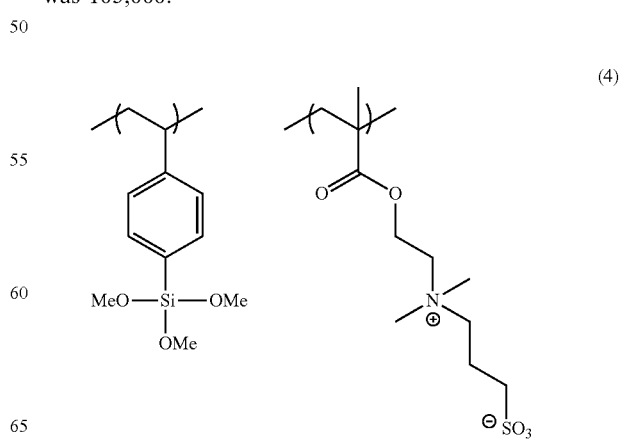

Production Example 8 Production of Modified Substrate with SPB-KBM-1403 Copolymer Trifluoroethanol (TFE) (137.8 mL) and the SPB-KBM-1403 copolymer synthesized in Production Example 7 were placed in a stainless steel reaction container for immersing an 8-inch silicon wafer equipped with a solvent circulation condenser and an ozone-cleaned 8-inch silicon wafer was immersed in the mixture for 24 hours at room temperature. Thereafter, the silicon wafer was washed with water and methanol, and was further immersed in water for 1 hour to obtain a SPB-KBM-1403 copolymer-modified silicon wafer (substrate).

Example 4 Production of Surface-Modified Silicon Wafer with Zwitterionic Polymer Chain (CMB-KBM-1403 Copolymer-Modified Substrate)

Production Example 9 Synthesis of CMB-KBM-1403 Copolymer

KBM-1403 (p-styryltrimethoxysilane, 0.175 g, 0.78 mmol) and CMB (N-methacryloyloxyethyl-N,N-dimethyl-ammonium-α-N-methylcarboxybetaine, 1.96 g, 9.1 mmol) were added to nitrogen-bubbled ethanol. AIBN (0.0905 g, 0.55 mmol) was added to the mixture and the polymerization was started at 70° C. AIBN (0.0181 g, 0.11 mmol) was added four hours later, and the reaction was further carried out for four hours to obtain a polymer having two structural units of Formula (5). The weight average molecular weight of the obtained polymer was 122,000.

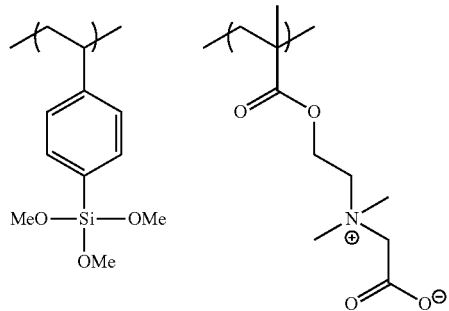

(5)

Production Example 10 Production of Modified Substrate with CMB-KBM-1403 Copolymer Ethanol (226.0 mL) and the CMB-KBM-1403 copolymer synthesized in Production Example 9 were placed in a stainless steel reaction container for immersing an 8-inch silicon wafer equipped with a solvent circulation condenser and an ozone-cleaned 8-inch silicon wafer was immersed in the mixture for 24 hours at room temperature. Thereafter, the silicon wafer was washed with water and methanol, and was further immersed in water for 1 hour to obtain a CMB-KBM-1403 copolymer-modified silicon wafer (substrate).

Example 5 Production of Surface-Modified Silicon Wafer with Zwitterionic Polymer Chain (CMB-MPTMS Copolymer-Modified Substrate)

Production Example 11 Synthesis of CMB-MPTMS Copolymer

The same procedure as the procedure in Production Example 9 was carried out except that KBM-1403 was replaced with MPTMS (3-methacryloyloxypropyltrimethoxysilane, 0.29 g, 1.0 mmol) to obtain a polymer having two structural units of Formula (6). The weight average molecular weight of the obtained polymer was 10,000.

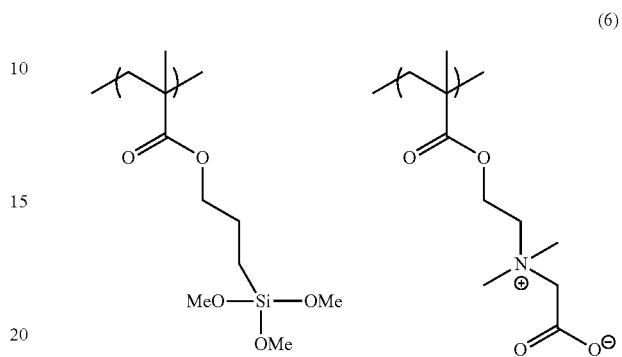

(6)

Production Example 12 Production of Modified Substrate with CMB-MPTMS Copolymer The same procedure as the procedure in Production Example 10 was carried out except that the CMB-MPTMS copolymer synthesized in Production Example 11 was used instead of the CMB-KBM-1403 copolymer in Production Example 10 to give a CMB-MPTMS copolymer-modified silicon wafer (substrate).

Comparative Example 1 Production of Surface-Modified Silicon Wafer with Polymer Chain Having No Zwitterion (B-PMA-Modified Substrate)

The same procedure as the procedure in Example 1 was carried out except that MA (methacrylic acid) was used instead of CMB in Example 1 to obtain a B-PMA-modified substrate (refer to schematic view of FIG. 1).

Comparative Example 2 Production of Surface-Modified Silicon Wafer with Polymer Chain Having No Zwitterion (B-PDMAEMA-Modified Substrate)

Figure 2:
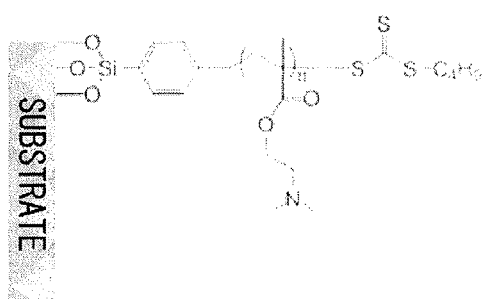
FIG. 2 is a schematic view illustrating a surface-modified substrate produced in Comparative Example 2.

The same procedure as the procedure in Example 1 was carried out except that DMAEMA (dimethylaminoethyl methacrylate) was used instead of CMB in Example 1 to obtain a B-PDMAEMA-modified silicon wafer (substrate) (refer to schematic view of FIG. 2).

Example 6 Production of Surface-Modified Silicon Oxynitride Wafer with Zwitterionic Polymer Chain (B-PCMB-Modified Substrate)

Production Example 13 Surface Modification of Silicon Oxynitride Wafer

An 8-inch silicon oxynitride wafer was washed with water, methanol, and acetone in this order and cleaned with UV/ozone.

Into a reaction container that can contain the 8-inch silicon oxynitride wafer, a solution in which 8 mL (2 v/v %) of CMPS (4-(chloromethyl)phenyltrimethoxysilane) was dissolved into 392 mL of toluene was charged, and the washed silicon oxynitride wafer was immersed into the solution under nitrogen atmosphere. The reaction container was placed in a water bath of 80° C. for 15 hours to react hydroxy groups on the surface of the silicon oxynitride wafer with alkoxysilyl groups of 4-(chloromethyl)phenyltrimethoxysilane. Thereafter, the silicon oxynitride wafer that was taken out was washed with toluene four times. After washing, the silicon oxynitride wafer was dried with flowing $N_2$ to obtain a silicon oxynitride wafer whose surface was modified with CMPS (refer to above Scheme 3: upper part).

Production Example 14 Surface Modification of Silicon Oxynitride Wafer with Zwitterionic Polymer Chain (Polymer Brush Type)

Using SDTB and tetrahydrofuran (THF) obtained in Production Example 1, 200 mL of 20 mg/mL SDTB solution was prepared and thereafter a silicon wafer whose surface was modified with CMPS was immersed into this solution and reacted at room temperature for 1 hour (refer to above Scheme 3: middle part).

Thereafter, the silicon oxynitride wafer was washed with THF and methanol and dried with flowing $N_2$.

The silicon oxynitride wafer whose surface was modified with dithiobenzoate as described above was placed in a reaction container that can contain the 8-inch silicon wafer. Into this reaction container, ethanol (600 mL) and N-methacryloyloxyethyl-N,N-dimethylammonium-α-N-methyl-carboxybetaine (CMB, 27.96 g, 120 mmol) were added. Subsequently, BSTMPA (B) (140.3 mg, 0.60 mmol) obtained in Production Example 2 and the water-soluble azo polymerization initiator V-501 (2,2'-azobis(2-methylpropionamidine)dihydrochloride, manufactured by Wako Pure Chemical Industries Ltd., 33.7 mg, 0.12 mmol) were added to the reaction solution. The resultant reaction solution was bubbled with $N_2$ for 30 minutes or more and the reaction container was sealed. The reaction container was placed in an oil bath of 70° C. and polymerization reaction was carried out for 24 hours (refer to above Scheme 3: lower part).

After completion of the polymerization reaction, the silicon oxynitride wafer was washed with methanol two times, water one time, and further methanol one time, and dried with flowing $N_2$ to obtain the silicon oxynitride wafer whose surface was modified with CMB polymer chains serving as zwitterionic polymer chains.

[Exposure Method]

The surface-modified silicon wafers produced in Examples and Comparative Examples were exposed to light of 250 mJ, 500 mJ, 1,000 mJ, and 3,000 mJ. Thereafter, the silicon wafers were washed with distilled water. Then, the wafers were used for a film thickness measurement, a contact angle measurement, a protein adsorption measurement, a patterning test (AFM measurement), and a protein patterning test (fluorescence microscope measurement).

NSR-5307E lens scanning stepper manufactured by Nikon Corporation (ArF excimer laser (wavelength: 193 nm)) was used for the exposure.

In the patterning test, the exposure was carried out through a mask that forms a pattern after development having vertical and horizontal widths of 0.25 μm to 5.0 μm.

[Film Thickness Measurement]

For the measurement of film thicknesses, the ellipsometric (polarization analysis) film thickness measurement device Lambda Ace RE-3100 (manufactured by Dainippon Screen Mfg. Co., Ltd.) was used.

The measured results of the film thicknesses (nm) of unexposed parts (exposed amount: 0 mJ) and exposed parts (exposed amount: 250 mJ to 3,000 mJ) of silicon wafers (substrates) produced in Example 1 to Example 5 and Comparative Example 1 and Comparative Example 2 are listed in Table 1.

TABLE 1

| | | Film thickness (nm) | | | | |
|---|---|---|---|---|---|---|
| | | Exposed amount (mJ) | | | | |
| | | 0 | 250 | 500 | 1,000 | 3,000 |
| Film Thickness (nm) | Example 1 | 6.84 | 5.29 | 4.45 | 4.11 | 3.29 |
| | Example 2 | 3.83 | 3.73 | 3.42 | 3.05 | 2.45 |
| | Example 3 | 2.95 | 2.71 | 2.28 | 2.13 | 1.78 |
| | Example 4 | 2.56 | 2.29 | 2.03 | 1.78 | 1.58 |
| | Example 5 | 2.66 | 2.72 | 2.53 | 2.23 | 1.84 |
| | Comparative Example 1 | 3.20 | 2.90 | 2.80 | 2.60 | 2.30 |
| | Comparative Example 2 | 5.80 | 4.30 | 3.60 | 3.10 | 3.00 |

As shown in Table 1, reduction in the film thicknesses was observed associated with increase in the exposed amount in each substrate produced in Example 1 to Example 5 and Comparative Example 1 and Comparative Example 2.

[Contact Angle Measurement]

The contact angles to water droplets were determined by a drop method using the contact angle meter (manufactured by Kyowa Interface Science Co., LTD., part No.: CA-D).

In the drop method, 3 μL to 4 μL of water was brought into contact with a sample (silicon wafer) under room temperature (relative humidity: about 50%) and the contact angle was evaluated as the total value of angles calculated by adding an angle formed 27 seconds after the contact and an angle formed 33 seconds after the contact. The evaluation was performed at 6 points in each wafer, and an average value of the total value was used as a measured value.

The measured results of the contact angles to water droplets of unexposed parts (exposed amount: 0 mJ) and exposed parts (exposed amount: 250 mJ to 3,000 mJ) of silicon wafers (substrates) produced in Example 1 to Example 5 and Comparative Example 1 and Comparative Example 2 are listed in Table 2.

TABLE 2

| | | Contact angle (degree) | | | | |
|---|---|---|---|---|---|---|
| | | Exposed amount (mJ) | | | | |
| | | 0 | 250 | 500 | 1,000 | 3,000 |
| Contact angle (degree) | Example 1 | 10.1 | 16.7 | 25.9 | 35.5 | 34.4 |
| | Example 2 | 10.8 | 11.8 | 17.3 | 25.5 | 28.5 |
| | Example 3 | 9.3 | 20.9 | 24.8 | 29.6 | 28.6 |
| | Example 4 | 30.5 | 37.8 | 40.0 | 40.0 | 35.6 |
| | Example 5 | 27.0 | 28.5 | 34.0 | 44.5 | 44.1 |
| | Comparative Example 1 | 65.0 | 55.0 | 57.0 | 56.0 | 51.0 |
| | Comparative Example 2 | 64.0 | 65.0 | 63.0 | 62.0 | 62.0 |

As shown in Table 2, increase in contact angles was observed associated with increase in the exposed amount in each substrate produced in Example 1 to Example 5. In contrast, increase in contact angles was not observed associated with increase in the exposed amount in each substrate produced in Comparative Example 1 and Comparative Example 2.

[Patterning Test (AFM Measurement)]

To the silicon wafers or the silicon oxynitride wafers whose surfaces were modified with polymer chains, which were produced in Example 1 to Example 6, exposure was carried out with 3,000 mJ by the above exposure method through a mask that forms a pattern having vertical and horizontal widths of 0.25 µm to 5.0 m after development. After the exposure, the pattern formation of the wafers was observed with an Atomic Force Microscope (AFM). In this observation, the high performance scanning probe microscope for large sample (Dimension ICON: manufactured by Bruker AXS, Inc.) was used and a single crystal Si (Bruker AXS, Inc.) was used as a probe. The measurement was carried out under conditions of a spring constant of about 3 N/m, a resonant frequency of 70 kHz, and a scan rate of 0.5 Hz. The pattern sizes (vertical and horizontal widths) of the observed grid patterns are listed in Table 3.

As shown in Table 3, formation of grid patterns was confirmed on the surfaces of the silicon wafers or the silicon oxynitride wafers whose surfaces were modified with the polymer chains, which were produced in Example 1 to Example 6.

TABLE 3

AFM measurement result

| | Pattern size (µm) |
|---|---|
| Example 1 | 4.3 |
| Example 2 | 5.5 |
| Example 3 | 5.7 |
| Example 4 | 5.6 |
| Example 5 | 5.0 |
| Example 6 | 0.25 |

[Protein Adsorption Measurement Test by Bicinchonianate (BCA) Method]

To unexposed parts (exposed amount: 0 mJ) and exposed parts (exposed amount: 250 mJ to 3,000 mJ) of silicon wafers (substrates) or silicon oxynitride wafers produced in Example 1 to Example 6 and Comparative Example 1 and Comparative Example 2, the adsorption test of Bovine Serum Albumin (BSA) was carried out for evaluation by a BCA method using an absorbance microplate reader.

First, each wafer was washed with Phosphate Buffered Saline (PBS) and a frame (inner diameter: 20 mm×20 mm, outer diameter: 25 mm×25 mm) fabricated using a silicone sheet was placed on the washed wafer. Inside of the silicone sheet frame, 500 µL of BSA solution (2 wt % in PBS, manufactured by Sigma-Aldrich Co. LLC.) was placed and incubated for 2 hours at room temperature. After removing the BSA solution, the inside of the frame was rinsed with PBS and thereafter 600 µL of a mixed solution of equal volume of "Micro BCA Protein Assay Kit" (trade name) (manufactured by Thermo Fisher Scientific K.K.)/PBS was added and the solution was incubated at 37° C. for 2 hours. The absorbance of the BCA solution after incubation was measured at a wavelength of 570 nm to determine the adsorbed amount (ng/cm$^2$) of BSA.

The obtained results are listed in Table 4.

TABLE 4

Adsorption amount (ng/cm$^2$)

| | | Exposed amount (mJ) | | | | |
|---|---|---|---|---|---|---|
| | | 0 | 250 | 500 | 1,000 | 3,000 |
| Adsorption amount (ng/cm$^2$) | Example 1 | 24.6 | 388.4 | 2,094.6 | 2,897.0 | 2,833.9 |
| | Example 2 | 88.9 | 264.7 | 707.9 | 827.7 | 968.1 |
| | Example 3 | 490.7 | 751.7 | 2,798.6 | 2,564.3 | 3,003.8 |
| | Example 4 | 153.7 | 1,171.2 | 1,678.3 | 1,620.7 | 1,838.4 |

TABLE 4-continued

Adsorption amount (ng/cm$^2$)

| | Exposed amount (mJ) | | | | |
|---|---|---|---|---|---|
| | 0 | 250 | 500 | 1,000 | 3,000 |
| Example 5 | 220.3 | 1,286.7 | 1,533.2 | 2,134.2 | 2,245.0 |
| Example 6 | 0 | 78.1 | 249.9 | 212.4 | 268.4 |
| Comparative Example 1 | 2,711.5 | 2,603.3 | 2,757.2 | 2,734.4 | 2,760.6 |
| Comparative Example 2 | 1,735.0 | 2,209.0 | 2,391.7 | 1,879.4 | 2,307.5 |

As shown in Table 4, increase in the adsorption amounts of BSA was observed associated with increase in the exposed amount in substrates produced in Example 1 to Example 6. In contrast, changes in the adsorption amounts of BSA were not observed associated with increase in the exposed amount in substrates produced in Comparative Example 1 and Comparative Example 2.

When the result of Example 1 was compared with that of Examples 2, the adsorption amount of BSA was larger in Example 1 in which the sample had phenyl groups in the polymer brush than in Example 2 in which the sample did not have phenyl groups.

The increasing ratio of the adsorption amount of BSA (as the number becomes larger, the increasing ratio becomes larger) was calculated using the formula of <Increasing ratio of adsorption amount of BSA> shown below for Example 4 and Example 5, and thus the value of the increasing ratio was larger in Example 4 in which the sample had phenyl groups in the polymer chains than in Example 5 in which the sample did not have phenyl groups.

From the above results, it was confirmed that sensitivity was improved by introducing the absorption moiety (such as phenyl groups) to the exposure light in the polymer brush or the polymer chains.

<Increasing Ratio of Adsorption Amount of BSA>

((Protein adsorption amount with high exposure (3,000 mJ))−(Protein adsorption amount with no exposure (0 mJ))/(Protein adsorption amount with no exposure (0 mJ))

Example 4; (1838.4−153.7)/153.7≈11.0

Example 5; (2245.0−220.3)/220.3≈9.2

[Protein Patterning Test]

Figure 3:
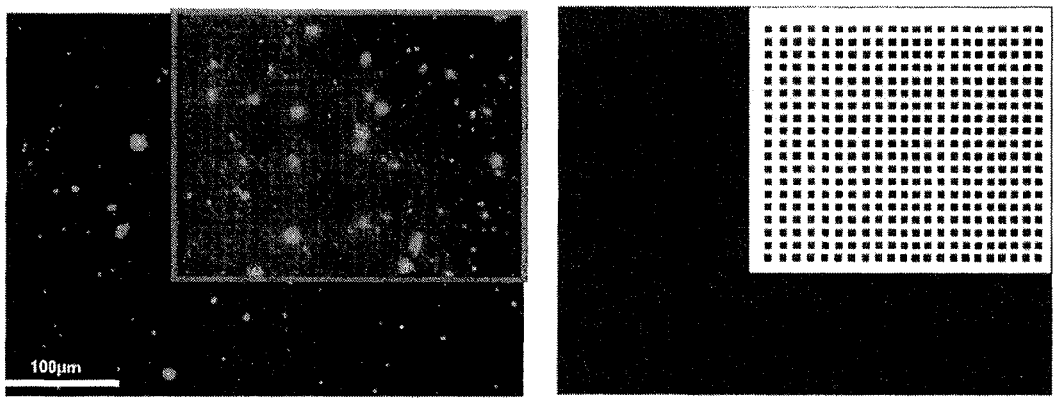
FIGS. 3A and 3B are photographs illustrating a protein patterning test results.

As described above, to the silicon wafer whose surface was modified with CMB polymer chains, which was produced in Example 1, exposure was carried out with 1,000 mJ through a mask that forms a pattern having vertical and horizontal widths of 5.0 µm (refer to schematic view of FIG. 3B). After the exposure, the specific adsorption of fluorescent material bonded immunoglobulin G (Molecular Probes (registered trademark) Alexa Fluor (registered trademark) 488-IgG (trade name), manufactured by Life Technologies Japan Ltd.) to the silicon wafer was observed by the fluorescence microscope (IX71 (trade name), Olympus Co., Ltd.). The observation photograph is illustrated in FIGS. 3A and 3B.

As illustrated in FIG. 3A (observation photograph), the specific adsorption of Alexa Fluor (registered trademark) 488-IgG (trade name) was observed in a grid shape so as to correspond to the white part (exposed part) of FIG. 3B (schematic view). The random bright spots in FIG. 3A are defective parts due to insufficient washing.

Similarly, when exposure was carried out with 3,000 mJ through a mask that forms a pattern having vertical and horizontal widths of 1.0 μm, the specific adsorption of Alexa Fluor (registered trademark) 488-IgG (trade name) having similar grid shape of 1.0 μm was observed.

[Evaluation of Cell Adhesion]

To the unexposed part (exposed amount: 0 mJ) and the exposed part (exposed amount: 250 mJ to 3,000 mJ) of the B-PCMB-modified substrate produced in Example 1, NIH-3T3 cells (Mouse skin-derived fibroblasts) (manufactured by DS Pharma Biomedical Co., Ltd.) were seeded so as to be $5\times10^4$ cell/cm$^2$, and the cells were cultured under 5% $CO_2$ atmosphere at 37° C. for 12 hours. Thereafter, the sample was washed with the phosphate buffer solution heated at 37° C. and the culture medium was replaced. After the cells were further cultured under 5% $CO_2$ atmosphere at 37° C. for 24 hours, the cells adhering onto the substrate were exposed to a culture liquid containing Cellstain (registered trademark) Hoechst 33342 (trade name) (2 μg/mL, manufactured by DOJINDO LABORATORIES) that was able to stain cell nuclei and Cellstain (registered trademark) Calcein-AM solution (trade name) (2 μg/mL, manufactured by DOJINDO LABORATORIES) that was able to stain cytoplasm of living cells for 30 minutes and thereafter the sample was washed with the phosphate buffer solution and observed with a fluorescence microscope. The cells adhering onto the substrate were measured by counting the number of stained cell nuclei. The area of the cells stained with the Calcein-AM solution was measured and an average cell spreading ratio per cell (%) was calculated by the formula below.

The cell adhesion was also carried out to the unexposed parts (exposed amount: 0 mJ) and the exposed parts (exposed amount: 250 mJ to 3,000 mJ) of the B-PMA-modified substrate produced in Comparative Example 1 and the B-PDMAEMA-modified substrate produced in Comparative Example 2 in the same operation as described above. The number of adhering cells was measured and the average cell spreading ratio per cell (%) was calculated.

<Average Spreading Ratio Per Cell (%)>

Average spreading ratio per cell (%)=[(Total area of total stained cells)/(Number of cells·cell nuclei)]/[Cross sectional area of non-adhering cells (397.4 μm$^2$)]×100

The obtained results are listed in Table 5 (the number of adhering cells) and Table 6 (the average cell spreading ratio (%)).

TABLE 5

| | | Number of adhering cells (cells/cm$^2$) | | | | |
|---|---|---|---|---|---|---|
| | | Exposed amount (mJ) | | | | |
| | | 0 | 250 | 500 | 1,000 | 3,000 |
| Number of adhering cells | Example 1 | 1,718 | 68,503 | 98,631 | 115,356 | 107,223 |
| | Comparative Example 1 | 81,448 | 100,578 | 105,161 | 99,204 | 82,708 |
| | Comparative Example 2 | 72,169 | 88,092 | 75,606 | 93,705 | 89,124 |

TABLE 6

| | | Average spreading ratio per cell (%) | | | | |
|---|---|---|---|---|---|---|
| | | Exposed amount (mJ) | | | | |
| | | 0 | 250 | 500 | 1,000 | 3,000 |
| Average spreading ratio | Example 1 | 143.8 | 332.0 | 350.8 | 335.2 | 312.1 |
| | Comparative Example 1 | 346.6 | 329.4 | 281.6 | 311.6 | 359.7 |
| | Comparative Example 2 | 245.7 | 340.9 | 300.7 | 323.7 | 342.6 |

As shown in Table 5 and Table 6, the result was obtained in which increase in the number of adhering cells on the substrate produced in Example 1 was observed associated with increase in the exposed amount. The average spreading ratio per cell showed a similar tendency.

In contrast, in the substrates produced in Comparative Example 1 and Comparative Example 2, the number of the adhering cells and the average spreading ratio per cell did not depend on the exposed amount.

The invention claimed is:

1. A light-degradable material comprising:
   a reaction starting terminal including a structure of Formula (1) that is capable of bonding to a surface of a substrate through a siloxane bond:

$(R_1O)_3$—Si—Y—     (1)

where $R_1$ is a saturated linear $C_{1-5}$ alkyl group; and
   Y is an optionally substituted phenylene group; and
   a linking part linked to the reaction starting terminal and including a structural unit of Formula (2-a) and/or Formula (2-b):

(2-a)

(2-b)

where $R_2$ to $R_4$ are each independently a saturated linear $C_{1-5}$ alkyl group;
   X is a hydrogen atom or a saturated linear $C_{1-5}$ alkyl group;
   Z is a carbanion (—COO$^-$ group) or a sulfo anion (—SO$_3^-$ group);
   Q is an ester bond group (—C(═O)—O— or —O—C(═O)—), a phosphodiester bond group (—O—P(═O)(—O$^-$)—O—), an amido bond group (—NH—CO— or —CO—NH—), a $C_{1-10}$ alkylene group, or an optionally substituted phenylene group or a combination of these divalent groups;

$m_1$ is an integer of 1 to 200, and
n is an integer of 1 to 10.

2. A light-degradable material comprising:
a polymer including a structural unit of Formula (2-a) and/or Formula (2-b) and a structural unit of styryltrimethoxysilane,

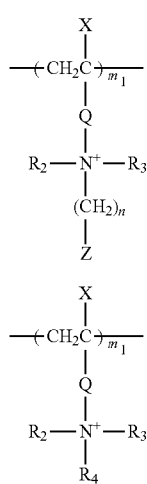

(2-a)

(2-b)

where $R_2$ to $R_4$ are each independently a saturated linear $C_{1-5}$ alkyl group;
X is a hydrogen atom or a saturated linear $C_{1-5}$ alkyl group;
Z is a carbanion (—COO⁻ group) or a sulfo anion (—SO$_3^-$ group);
Q is an ester bond group (—C(=O)—O— or —O—C(=O)—), a phosphodiester bond group (—O—P(=O)(—O⁻)—O—), an amido bond group (—NH—CO— or —CO—NH—), a $C_{1-10}$ alkylene group, or an optionally substituted phenylene group or a combination of these divalent groups;
$m_1$ is an integer of 1 to 200; and
n is an integer of 1 to 10.

3. The light-degradable material according to claim 1, wherein
the light-degradable material is a material for pattern formation by photolithography.

4. The light-degradable material according to claim 3, wherein
the photolithography is carried out using an ArF excimer laser.

5. The light-degradable material according to claim 1, wherein
Q is a combination of the ester bond group (—C(=O)—O— or —O—C(=O)—) and the $C_{1-10}$ alkylene group or a combination of the phosphodiester bond group (—O—P(=O)(—O⁻)—O—) and the $C_{1-10}$ alkylene group.

6. The light-degradable material according to claim 3, wherein
the light-degradable material is a material for forming a pattern in which proteins, cells, or viruses are specifically adsorbed.

7. A substrate that is capable of forming a pattern, obtained by bonding the light-degradable material as claimed in claim 1 to a surface of the substrate through siloxane bonds.

8. The substrate according to claim 7, wherein
the substrate is a substrate on which a pattern is formed by carrying out pattern exposure on the light-degradable material bonded to the surface of the substrate by a photolithography method.

9. The substrate according to claim 8, wherein
the exposure is carried out using an ArF excimer laser.

10. The substrate according to claim 7, wherein
the substrate is a glass substrate, a metal substrate, a metal oxide substrate, a metal nitride substrate, a metal carbide substrate, a metal oxynitride substrate, a ceramic substrate, a silicon oxide substrate, a silicon nitride substrate, a silicon carbide substrate, a silicon oxynitride substrate, or a silicon substrate.

11. A substrate for cell culture, made by using the substrate as claimed in claim 7.

12. A microflow channel made by using the substrate as claimed in claim 7.

13. A method of producing a patterned substrate to which proteins, cells, or viruses are specifically adsorbed, the method comprising:
producing a surface-modified substrate by fixing the light-degradable material as claimed in claim 1 to a surface of the substrate through siloxane bonds;
forming a pattern on the surface of the substrate by carrying out pattern exposure on the surface-modified substrate; and
carrying out adsorption/adhesion of proteins, cells, or viruses on a part of the surface of the substrate where the pattern exposure has been carried out.

14. The method for producing the patterned substrate according to claim 13, wherein
the pattern exposure is carried out using an ArF excimer laser.

15. The method for producing the patterned substrate according to claim 13, wherein
the pattern formed substrate is a substrate for cell culture.

16. The method for producing the patterned substrate according to claim 13, wherein
the pattern formed substrate is a substrate for microflow channel formation.

17. A method of producing a patterned substrate to which proteins, cells, or viruses are specifically adsorbed, the method comprising:
producing a surface-modified substrate by fixing a light-degradable material to a surface of the substrate through siloxane bonds;
forming a pattern on the surface of the substrate by carrying out pattern exposure on the surface-modified substrate using an ArF excimer laser; and
carrying out adsorption/adhesion of proteins, cells, or viruses on a part of the surface of the substrate where the pattern exposure has been carried out,
wherein the light-degradable material comprises:
a reaction starting terminal including a structure of Formula (1) that is capable of bonding to a surface of a substrate through a siloxane bond:

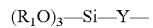

(1)

where $R_1$ is a saturated linear $C_{1-5}$ alkyl group; and
Y is a sulfur atom, a dithiocarbonic acid ester bond group (—S—C(=S)—), a trithiocarbonic acid ester bond group (—S—C(=S)—S—), a $C_{1-10}$ alkylene group, or an optionally substituted phenylene group or a combination of these divalent groups; and a linking part linked to the reaction starting terminal and including a structural unit of Formula (2-a) and/or Formula (2-b):

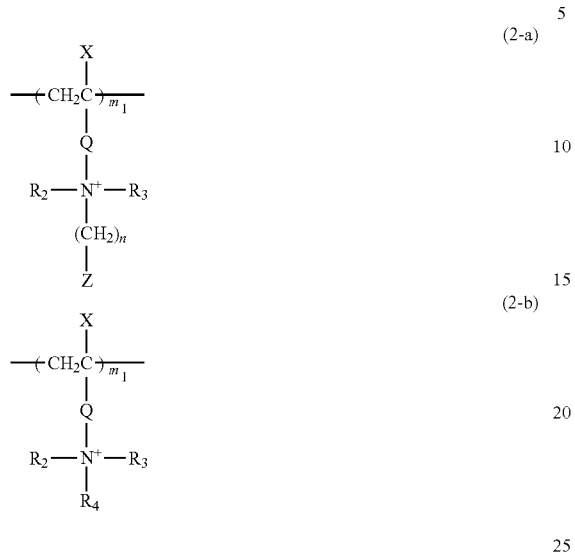

where $R_2$ to $R_4$ are each independently a saturated linear $C_{1-5}$ alkyl group;
X is a hydrogen atom or a saturated linear $C_{1-5}$ alkyl group;
Z is a carbanion (—COO⁻ group) or a sulfo anion (—SO$_3^-$ group);
Q is an ester bond group (—C(=O)—O— or —O—C(=O)—), a phosphodiester bond group (—O—P(=O)(—O⁻)—O—), an amido bond group (—NH—CO— or —CO—NH—), a $C_{1-10}$ alkylene group, or an optionally substituted phenylene group or a combination of these divalent groups;
$m_1$ is an integer of 1 to 200, and
n is an integer of 1 to 10.

18. A method of producing a patterned substrate to which proteins, cells, or viruses are specifically adsorbed, the method comprising:
producing a surface-modified substrate by fixing a light-degradable material to a surface of the substrate through siloxane bonds;
forming a pattern on the surface of the substrate by carrying out pattern exposure on the surface-modified substrate; and
carrying out adsorption/adhesion of proteins, cells, or viruses on a part of the surface of the substrate where the pattern exposure has been carried out,
wherein the light-degradable material comprises:
a polymer including a structural unit of Formula (2-a) and/or Formula (2-b) and a structural unit of Formula (3-1) having a side chain being capable of bonding to a surface of a substrate through a siloxane bond or a structural unit derived from styryltrimethoxysilane or 3-methacryloyloxypropyltrimethoxysilane,

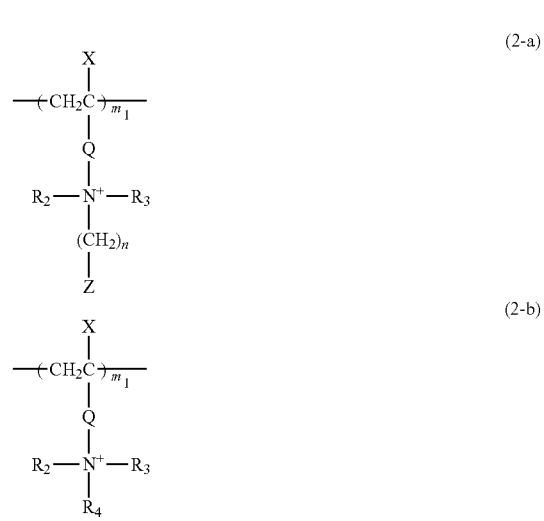

where $R_2$ to $R_4$ are each independently a saturated linear $C_{1-5}$ alkyl group;
X is a hydrogen atom or a saturated linear $C_{1-5}$ alkyl group;
Z is a carbanion (—COO⁻ group) or a sulfo anion (—SO$_3^-$ group);
Q is an ester bond group (—C(=O)—O— or —O—C(=O)—), a phosphodiester bond group (—O—P(=O)(—O⁻)—O—), an amido bond group (—NH—CO— or —CO—NH—), a $C_{1-10}$ alkylene group, or an optionally substituted phenylene group or a combination of these divalent groups;
$m_1$ is an integer of 1 to 200; and
n is an integer of 1 to 10, and

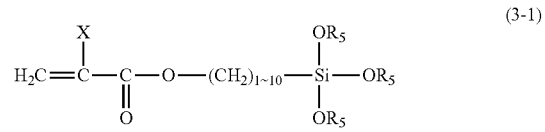

where $R_5$ is a saturated linear $C_{1-5}$ alkyl group; and
X is a hydrogen atom or a saturated linear $C_{1-5}$ alkyl group.

* * * * *